United States Patent [19]

Shelley

[11] Patent Number: 5,217,499
[45] Date of Patent: Jun. 8, 1993

[54] RIM-BEARING ACETABULAR COMPONENT OF HIP JOINT PROSTHESIS

[75] Inventor: Philip Shelley, Laughton Enlemouthern, Great Britain

[73] Assignee: Minnesota Mining and Manufacturing Company, St. Paul, Minn.

[21] Appl. No.: 702,103

[22] Filed: May 15, 1991

Related U.S. Application Data

[63] Continuation of Ser. No. 394,801, Aug. 16, 1989, abandoned.

[30] Foreign Application Priority Data

Aug. 17, 1988 [GB] United Kingdom ............... 8819587

[51] Int. Cl.5 .......................... A61F 2/30; A61F 2/34; A61F 1/04
[52] U.S. Cl. ...................... 623/22; 606/89; 606/86; 623/18
[58] Field of Search ....... 623/16, 18, 19, 20, 623/22, 23; 606/86, 89, 90, 99, 91

[56] References Cited

U.S. PATENT DOCUMENTS

| | | | |
|---|---|---|---|
| 3,698,017 | 10/1972 | Scales et al. | 623/22 |
| 3,722,002 | 3/1973 | Charnley | 3/1 |
| 3,882,550 | 5/1975 | Karpf et al. | 3/1 |
| 3,903,549 | 9/1975 | Deyerle | 623/22 |
| 3,918,102 | 11/1975 | Eichlet | 623/22 |
| 3,982,281 | 9/1976 | Giliberty | 623/22 |
| 4,173,797 | 11/1979 | Langlais et al. | 623/22 |
| 4,180,873 | 1/1980 | Fixel | 623/22 |
| 4,285,071 | 8/1981 | Nelson et al. | 623/22 |
| 4,437,193 | 3/1984 | Oh | 623/22 |
| 4,563,778 | 1/1986 | Roche et al. | 623/22 |
| 4,596,580 | 6/1986 | Weill | 623/22 |
| 4,632,111 | 12/1986 | Roche | 128/303 R |
| 4,828,565 | 5/1989 | Duthoit et al. | 623/22 |

FOREIGN PATENT DOCUMENTS

| | | |
|---|---|---|
| 0022308 | 1/1981 | European Pat. Off. . |
| 0065482 | 11/1982 | European Pat. Off. . |
| 0118194 | 9/1984 | European Pat. Off. . |
| 0120595 | 10/1984 | European Pat. Off. . |
| 0142759 | 5/1985 | European Pat. Off. . |
| 0179736 | 4/1986 | European Pat. Off. . |
| 2845231 | 5/1979 | Fed. Rep. of Germany . |
| 3310944 | 10/1984 | Fed. Rep. of Germany ........ 623/22 |
| 8701242 | 4/1987 | Fed. Rep. of Germany . |
| 2194123 | 2/1974 | France .................. 623/22 |
| 663893 | 1/1988 | Switzerland . |
| 0483980 | 9/1977 | U.S.S.R. ................. 623/22 |
| 1304626 | 1/1973 | United Kingdom . |
| 1499463 | 2/1978 | United Kingdom . |
| 2080118 | 2/1982 | United Kingdom . |
| 88195870 | 8/1988 | United Kingdom . |

OTHER PUBLICATIONS

Socket Fixation using a Metal-backed Acetabular Component for Total Hip Replacement; The Journal of Bone and Joint Surgery, vol. 64-A; pp. 745-748.
Stress Distributions in the Acetabular Region I. Before and After Total Joint Replacement; 15 J. Biomechanics 155-164 (Pergamon Press Ltd. 1982).
Stress Distributions in the Acetabular Region II. Effects of Cement Thickness and Metal Backing of the Total Hip Acetabular Component, 15 J. Biomechanics pp. 165-170 (Pergamon Press 1982).
Advances in Total hip Replacement by W. Harris.

Primary Examiner—David Isabella
Attorney, Agent, or Firm—Gary L. Griswold; Walter N. Kirn; Jeffrey J. Hohenshell

[57] ABSTRACT

An acetabular implant for a hip joint prosthesis comprising a metal cup shell (2) adapted to be secured in the acetabulum of a patient. The metal cup shell (2) has a hemispherical cavity (6) into which a liner may be inserted to provide a spherical bearing surface for the ball portion of the hip joint. Screws (26, 28) may be inserted through three apertures (20, 22 and 24) in the metal cup shell (2) into the ilium, ischium and pubic ramus of the patient. A continuous circumferential flange (8) is provided around the opening of the cavity (6). The flange (8) has an outside diameter which is at least 10% greater than the outside diameter of the remainder of the metal cup shell (2) at its widest point. The circumferential flange (8) provides a bearing surface (10) for contacting the rim (12) of the acetabulum of the patient when the metal cup shell (2) is fitted.

7 Claims, 4 Drawing Sheets

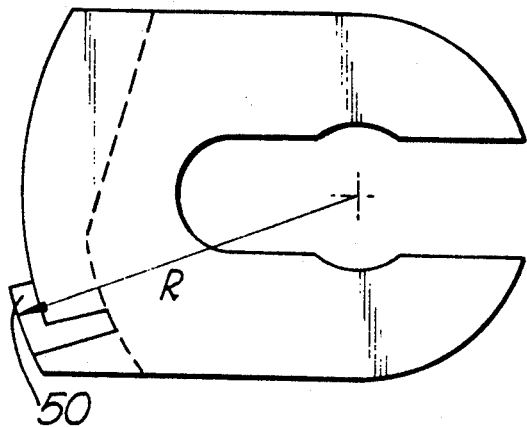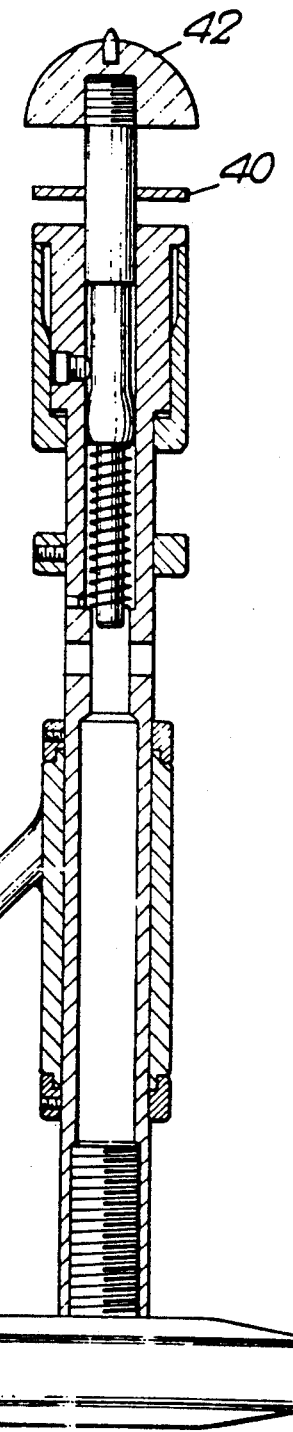

RIM-BEARING ACETABULAR COMPONENT OF HIP JOINT PROSTHESIS

This is a continuation of application Ser. No. 07/394,801 filed Aug. 16, 1989 now abandoned.

FIELD OF THE INVENTION

This invention relates to a hip joint prosthesis and in particular to the acetabular component of a hip joint prosthesis.

BACKGROUND TO THE INVENTION

Prosthesis for the replacement of hip joints are well known. Originally, only the ball-end on the head of the femur could be replaced but it has since proved possible to replace either part of the hip joint i.e. the acetabular socket of the joint or the ball-end on the femur.

Known acetabular cup implants, which form the socket portion of an artificial hip joint, comprise a metal cup shell, which is secured within a cavity in the pelvic bone of a patient, and an inner liner of plastic material which provides a spherical bearing surface for receiving the ball portion of the joint. The metal cup shell may be provided with an external thread to facilitate anchorage to the pelvic bone or may be secured by other means such as cement or screws.

Most current designs of metal cup shells can be grouped into two basic profiles, frusto-conical and hemispherical, since these shapes may be conveniently fabricated by rotating reamers. In all cases the designs rely upon the floor and internal walls of the acetabulum for anchorage and to transmit the forces to which the joint is subjected.

There are several designs of acetabular cup implants which comprises a continuous or discontinuous circumferential flange around the opening of the cup implant. U.S. Pat. No. 4,563,778 discloses an acetabular cup assembly having a circumferential flange. That cup assembly is adapted to be secured to bone tissue with bone cement. U.S. Pat. No. 3,982,281 discloses an acetabular cup assembly having a circumferential flange. That cup assembly is inserted into the acetabulum so that there is initially clearance between the flange and the bone structure to allow settling movement in the device before the flange contacts the bone. U.S. Pat. No. 4,180,873 discloses a frusto-conical cup shell having a circumferential flange which is force fitted into a prepared bone void of the acetabulum.

It is an anatomical fact that the thickest and strongest section of the pelvis in the acetabular region is the rim of the acetabulum. However, this rim presents an uneven and irregular margin which has precluded its use for load bearing in a hip joint prosthesis. It has now been found that by smoothing the rim of the acetabulum and providing a metal cup shell with a flange which bears on the machined surface the potential load bearing capacity of the rim of the acetabulum can be effectively utilized in addition to the internal surfaces of the acetabulum.

SUMMARY OF THE INVENTION

Therefore according to one aspect of the present invention there is provided an acetabular implant for a hip joint prosthesis comprising a metal cup shell adapted for securing in the acetabulum of a patient. The metal cup shell has a cavity into which a liner may be inserted to provide a spherical bearing surface for the ball portion of the hip joint. The metal cup shell includes a circumferential flange around the opening of the cavity, and three screw-receiving apertures positioned for insertion of screws into the ilium, ischium and pubic ramus of the patient. The flange has an outside diameter which is at least 10% greater than the outside diameter of the remainder of the metal cup shell at its widest point. The circumferential flange provides a bearing surface for contacting the rim of the acetabulum of the patient when the metal cup shell is fitted.

Other features will be pointed out hereinafter.

BRIEF DESCRIPTION OF THE DRAWINGS

The invention will now be described with reference to the accompanying drawings in which:

FIGS. 4 and 5 represent a reaming tool and blade for reaming the rim of the acetabulum.

Corresponding reference characters indicate corresponding parts throughout the several views of the drawings.

DETAILED DESCRIPTION OF PREFERRED EMBODIMENTS

Figure 1:
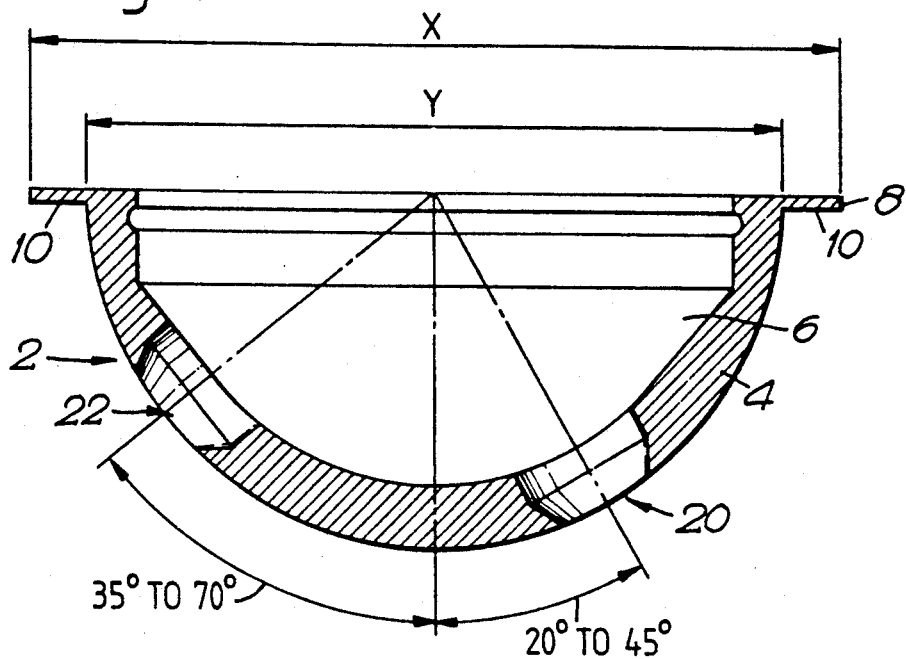
FIG. 1 represents a cross-section through a metal shell cup in accordance with the invention.
Figure 2:
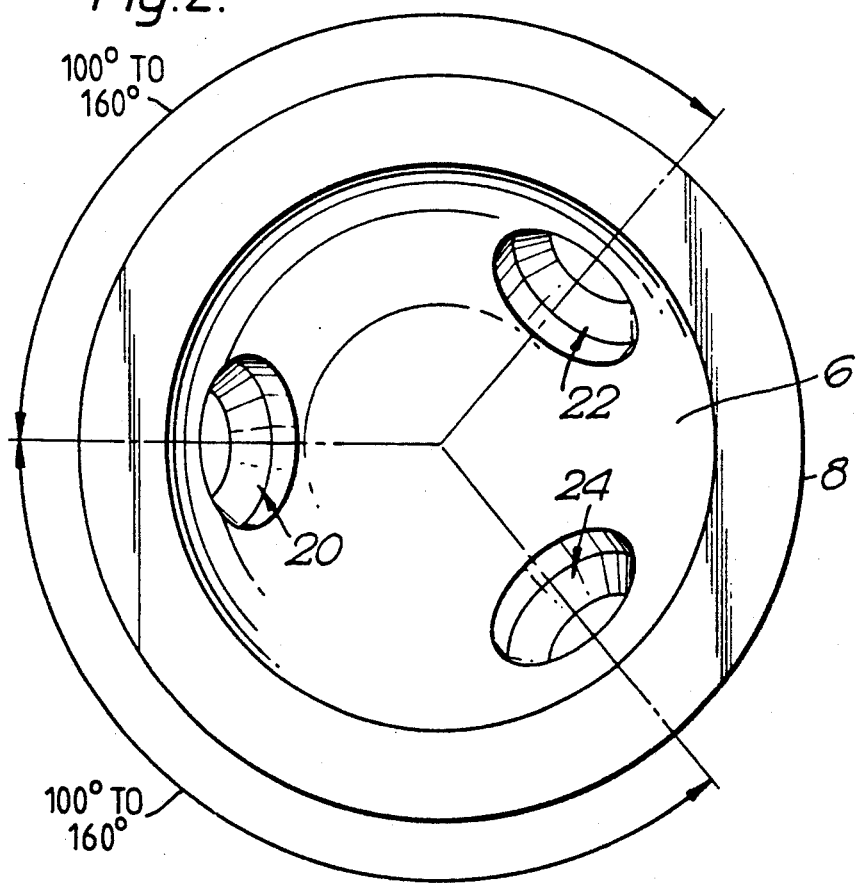
FIG. 2 represents a plan view of a shell cup in accordance with the invention.
Figure 3:
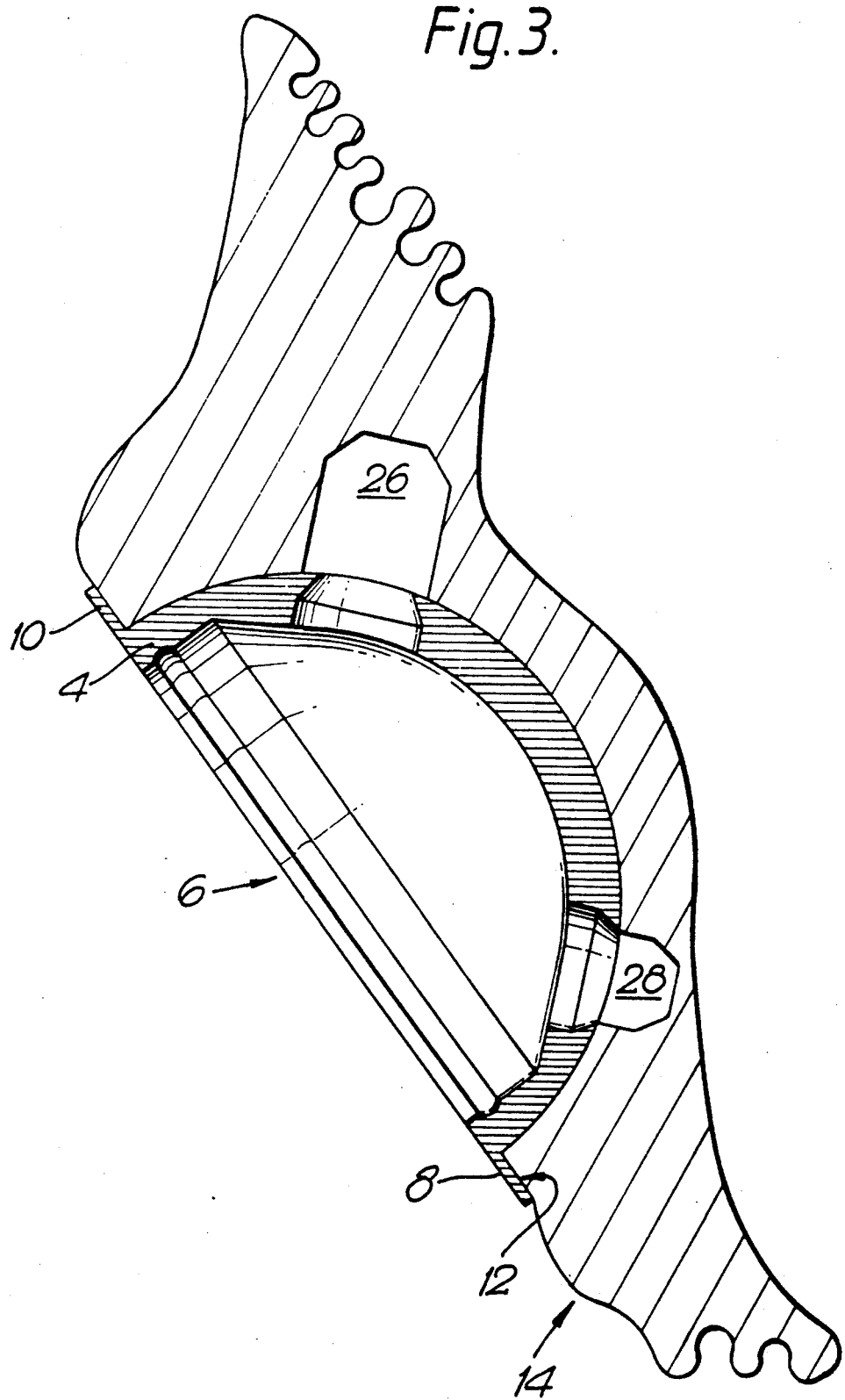
FIG. 3 represents a section through an acetabulum showing a metal shell cup anchored to the pelvic bone.

Referring to FIGS. 1 to 3 the metal cup shell 2 comprises a substantially hemispherical body 4 defining a hemispherical cavity 6. The shell 2 includes a circumferential flange 8 having a diameter 'X' which is from 10 to 40% greater than the diameter 'Y', the widest outside diameter of the remainder of the metal cup shell 2. The flange 8 has a bearing surface 10 which bears against the required surface 12 of the rim of the acetabulum when the cup shell 2 is fitted (see FIG. 3). The cup shell 2 is preferably fabricated from titanium or a titanium alloy including aluminium or vanadium.

The circumferential flange 8 of the metal cup shell 2 provides an effective means of transmitting forces in the hip joint to the pelvic bone thereby reducing stresses in other parts of the joint. The circumferential flange 8 generally has an outside diameter which is from 10–40% greater than that of the remainder of the metal cup shell 2, preferably 20–40% greater.

The bearing surface 10 of the circumferential flange 8 is preferably planar and at a right angle to the longitudinal axis of the hemispherical cavity 6, although the plane of the bearing surface 10 may be slightly inclined with respect to the longitudinal axis of the cavity. The bearing surface 10 may also be frusto-conical or curved. The flange 8 is preferably continuous to provide maximum transmission of forces to the pelvic bone but some discontinuities are permissible e.g. slits or notches.

The metal cup shell 2 is secured to the acetabulum by conventional techniques, e.g., cement, screw thread on the outer surface or screws passing through the shell 2. In order to maximize the diameter and length of the screws (and the anchorage of the metal cup shell 2), the arrangement is to use three screws projecting into the ilium, ischium and pubic ramus of the patient. The metal cup shell 2 has three apertures 20, 22 and 24 for accepting such screws 26 and 28 drilled at the correct angles for optimum positioning, and the screws 26 and 28 may readily be inserted through a guide to ensure accurate positioning.

The following configuration of apertures 20, 22 and 24 and positioning of the screws 26 and 28 is believed to be particularly useful:

When viewed in plan (FIG. 2) the angle A, A' formed between a line passing through the center of the aperture 20 for the superior screw 26 and the center line of the cavity and a line passing through the center of an aperture 22 or 24 for an inferior screw 28 and the center of the cavity is in the range 100 to 160°; preferably the apertures are positioned at 0°, 130° and 230°;

In the side view (FIG. 1) the angle formed between the longitudinal axis of the hemispherical cavity 6 and the longitudinal axis of the aperture 20 for the superior screw 26 is from 20 to 45°, preferably 30°, and the angle formed between the longitudinal axis of an aperture 22 or 24 for an inferior screw 28 and the longitudinal axis of the cavity 6 is from 35° to 75°, preferably 50°.

FIGS. 1 to 3 also illustrate the configuration of apertures 20, 22 and 24 and screws 26 and 28 for optimum fixing of the metal cup shell 2 within the pelvic bone 14 (FIG. 3). The centers of apertures 22 and 24 for the inferior screws 28 are arranged as shown in FIG. 2 forming angles of from 100 to 160°(preferably 130°) on either side of the aperture 20 for the superior screw 26. When viewed in cross-section as in FIG. 1, the longitudinal axis of the aperture 20 for the superior screw 26 forms an angle of from 20 to 45° with the longitudinal axis of the cavity 6 and those for the inferior screws 28 form an angle of from 35 to 70°.

In order to ensure good fitting of the metal cup shell 2, the acetabulum must be reamed in the conventional manner and the rim 12 of the acetabulum must be shaved or reamed to provide a mating surface 12 for the bearing surface 10 of the flange 8. FIG. 4 illustrates a reaming tool comprising a blade 40 for shaving the rim 12 of the acetabulum. The end 42 of the tool comprises a centralizing body which is inserted in the acetabulum and the instrument rotated so that the blade 40 shaves the rim 12 of the acetabulum to provide a smooth surface 12. An example of a suitable blade is shown in FIG. 5. The blade 40 has a cutting edge 50 and a radius R which is selected to be at least one half the diameter of the flange 8.

Figure 6:
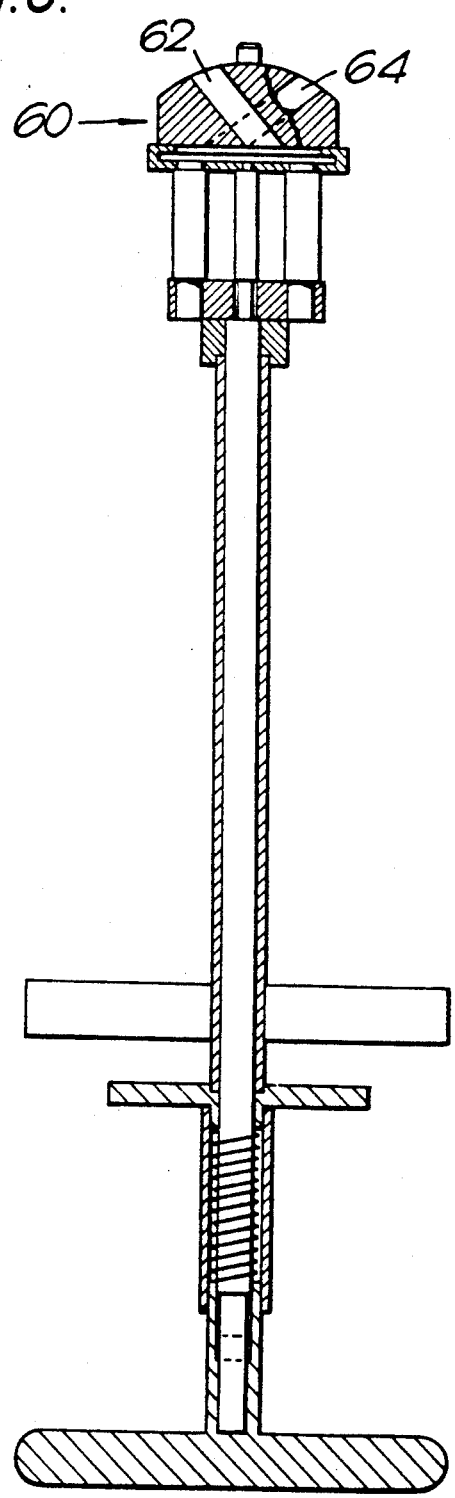
FIG. 6 represents an alignment guide for inserting screws through the metal cup shell into the pelvic bone.

The screws 26, 28 may readily be inserted through the apertures 20, 22 and 24 in correct alignment using the guide shown in FIG. 6. The guide includes an insert 60. The insert 60 is positioned within the metal cup shell 2, and three holes are drilled in appropriate alignment with respect to the pelvic bone for the desired positioning of the screws 26 and 28. The holes have diameters comparable to the outside diameter of the screws 26, 28. The holes 62, 64 of the guide are aligned with the apertures 20, 22 and 24 in the metal cup shell 2, and the screws 26, 28 are inserted in the respective holes in the guide and driven into the pelvic bone 14 to securely anchor the metal cup shell 2. The superior screw 26 is driven into the ilium, and the inferior screws 28 are driven into the ischium and pubic ramus.

The metal cup shell 2 may be used with conventional plastic and/or ceramic inserts to provide the spherical bearing surface for the ball of the joint. The metal cup shell 2 may also conform to the configuration of that disclosed in our corresponding British Patent Application No. 8819589.0 (incorporated herein by reference), which describes an acetabular implant comprising a metal cup shell adapted to be secured to the pelvic bone of a patient, and a plastic insert for receiving the ball portion of a hip joint. A hemispherical cavity of the metal cup shell and the outer surface of the plastic insert are dimensioned to allow an interference fit of the plastic insert within the cavity at the body temperature of the patient. The surface of the metal shell defining the cavity is provided with one or more apertures or grooves into which the plastic material of the insert may flow when the insert is fitted to provide a mechanical interlock between the insert and cup shell, thereby securing the insert against rotational and distraction forces relative to the metal cup shell. The apertures may conveniently take the form of a concentric or annular groove near the opening of the hemispherical cavity and one or more "radial" grooves.

As various changes could be made in the above constructions and methods without departing from the scope of the invention, it is intended that all matter contained in the above description or shown in the drawings shall be interpreted as illustrative and not in a limiting sense.

I claim:

1. A kit for use in a hip joint prosthesis comprising, in combination, an acetabular implant comprising a metal cup shell adapted to be secured in the acetabulum of a patient, the metal cup shell defining a generally hemispherical cavity having an opening into which a liner may be inserted to provide a spherical bearing surface for the ball portion of the hip joint, the metal cup shell comprising walls defining three apertures positioned for insertion therethrough of screws into the ilium, ischium and pubic ramus of the patient, and a continuous circumferential flange extending generally radially outwardly adjacent the opening of the cavity, the flange having an outside diameter that is from 10 to 40 percent greater than the out side diameter of the remainder of the metal cup shell at its widest point, the circumferential flange providing a bearing surface adapted for contacting a rim of the acetabulum of the patient when the metal cup shell is fitted; and a reaming tool comprising a blade for shaving the rim of the acetabulum; and a guide comprising an insert having an arcuate end surface, said guide having walls defining three holes positioned at guide screws through the three apertures of the metal cup shell and into the ilium, ischium and pubic ramus of the patient.

2. A combination according to claim 1 wherein said blade has a cutting edge and radius that is at least one half the diameter of the continuous circumferential flange.

3. A combination according to claim 1 in which the outside diameter of the flange is from 20 to 40 percent greater than the outside diameter of the remainder of the metal cup shell at its widest point.

4. A combination according to claim 1 in which the bearing surface of the flange is planar and substantially at a right angle to the longitudinal axis of the cavity.

5. A combination according to claim 1 in which the bearing surface of the flange is frusto-conical.

6. A combination according to claim 1 wherein walls of the metal cup shell define the three apertures such that they are adapted to receive one superior screw for insertion into the ilium of the patient and two inferior screws for insertion into the ischium and pubic ramus of the patient, the three apertures being arranged such that;

when viewed along the longitudinal axis of the hemispherical cavity, first angles of approximately 100-160 degrees are formed between a line through the center of the aperture of the superior screw and the longitudinal axis of the cavity and the lines through the centers of the apertures for the inferior screws and the longitudinal axis of the cavity; and when viewed in a direction perpendicular to the longitudinal axis of the hemispherical cavity, a second angle of approximately 20-45 degrees is formed between the center line of the aperture for the superior screw and the longitudinal axis of the cavity, and third angles of approximately 35-70 degrees are formed between the longitudinal axis of the cavity and the center lines of the apertures for the inferior screws.

7. A combination according to claim 6 wherein the three apertures are arranged such that:

when viewed along the longitudinal axis of the hemispherical cavity, the first angles are approximately 130 degrees; and when viewed in a direction perpendicular to the longitudinal axis of the hemispherical cavity, the second angle is approximately 30 degrees, and the third angles approximately 50 degrees.

* * * * *

UNITED STATES PATENT AND TRADEMARK OFFICE
CERTIFICATE OF CORRECTION

PATENT NO. : 5,217,499
DATED : June 8, 1993
INVENTOR(S) : Philip Shelley

It is certified that error appears in the above-indentified patent and that said Letters Patent is hereby corrected as shown below:

Col. 4, line 37, delete "out side" insert --outside--.

Col. 4, line 46, delete "at" insert --to--.

Signed and Sealed this

Twenty-second Day of February, 1994

Attest:

BRUCE LEHMAN

Attesting Officer

Commissioner of Patents and Trademarks